United States Patent [19]

Minetola et al.

[11] Patent Number: 5,246,431
[45] Date of Patent: Sep. 21, 1993

[54] DIAPER WITH SOURCE REDUCTION OVERLAY AND HAVING IMPROVED FECAL CONTAINMENT CHARACTERISTICS

[75] Inventors: James A. Minetola, Peachtree City; L. Jane Weeks; M. Carletta Shelhorse, both of Newnan, all of Ga.

[73] Assignee: Pope & Talbot Company, Shenandoah, Ga.

[21] Appl. No.: 710,993

[22] Filed: Jun. 6, 1991

Related U.S. Application Data

[63] Continuation-in-part of Ser. No. 472,052, Jan. 31, 1990, abandoned.

[51] Int. Cl.⁵ .................. A61F 13/15; A61F 13/20
[52] U.S. Cl. .................. 604/385.2; 604/385.1; 604/378
[58] Field of Search .............. 604/385.2, 385.1, 398

[56] References Cited

U.S. PATENT DOCUMENTS

| | | |
|---|---|---|
| 3,842,838 | 10/1974 | Gellert ............................. 604/365 |
| 4,037,602 | 7/1977 | Hawthorne ................ 604/385.1 X |
| 4,636,207 | 1/1987 | Buell . |
| 4,657,539 | 4/1987 | Hasse . |
| 4,695,278 | 9/1987 | Lawson . |
| 4,704,116 | 11/1987 | Enloe . |
| 4,738,677 | 4/1988 | Foreman . |
| 4,743,246 | 5/1988 | Lawson . |
| 4,795,452 | 1/1989 | Blaney . |
| 4,795,454 | 1/1989 | Dragoo . |
| 4,808,177 | 2/1989 | DesMarais et al. .......... 604/385.2 X |
| 4,808,178 | 2/1989 | Aziz . |
| 4,816,025 | 3/1989 | Foreman ..................... 604/385.2 |
| 4,822,435 | 4/1989 | Igaue et al. .................. 604/385.2 X |
| 4,834,740 | 5/1989 | Suzuki . |
| 4,834,742 | 5/1989 | Wilson . |
| 4,842,596 | 6/1989 | Kielpikowski . |
| 4,846,823 | 7/1989 | Enloe . |
| 4,846,825 | 7/1989 | Enloe . |
| 4,892,528 | 1/1990 | Suzuki et al. ................. 604/385.2 |
| 4,904,251 | 2/1990 | Igaue et al. .................. 604/385.2 |
| 5,061,260 | 10/1991 | Callahan et al. ................. 604/378 |

Primary Examiner—Randall L. Green
Assistant Examiner—Elizabeth M. Burke
Attorney, Agent, or Firm—Francis J. Bouda

[57] ABSTRACT

An absorbent disposable sanitary product such as a disposable baby diaper has an absorbent core and a multi-ply body-contacting topsheet. The construction of the diaper reduces raw material consumption and also waste at the source of manufacture and, therefore, is environmentally attractive. One of the plys of the topsheet contacts the body but not the core, and another contacts the absorbent core, as well as the body, with a space between the plys. The body-contacting ply has a plurality of upstanding cuffs which improve fecal containment, and the space between the plys reduces wet-back. The thickness of the multi-ply body-contacting topsheet is less than the thickness of conventional, single ply, nonwoven topsheets.

15 Claims, 2 Drawing Sheets

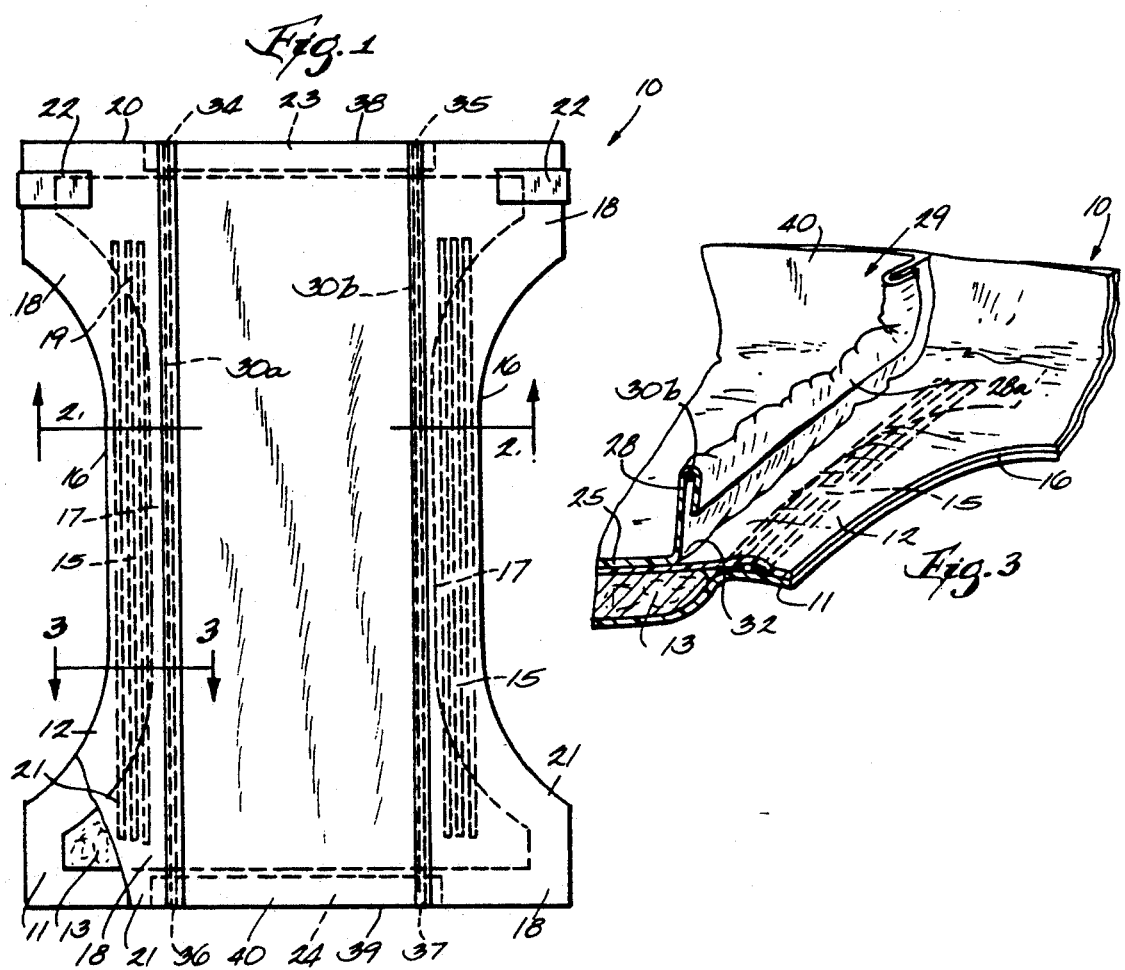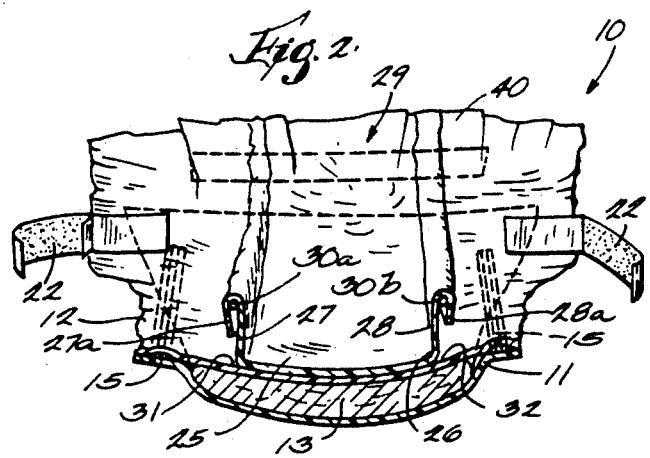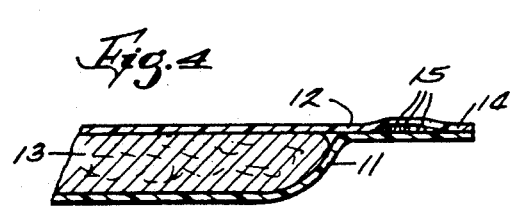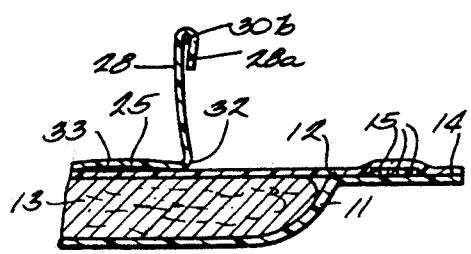

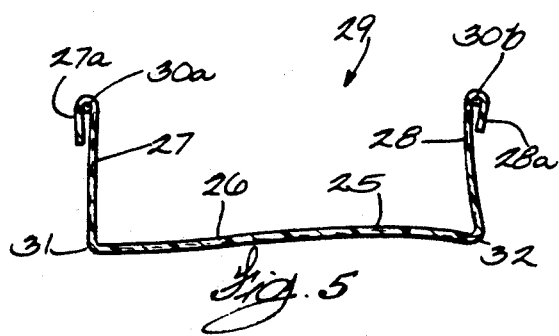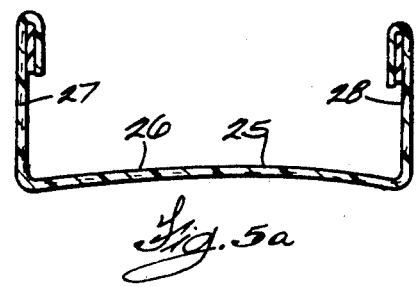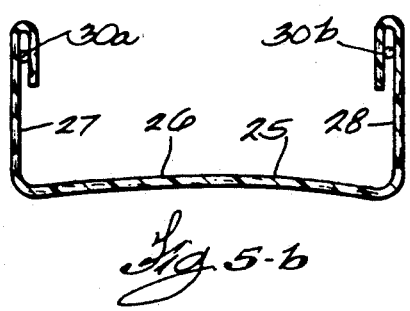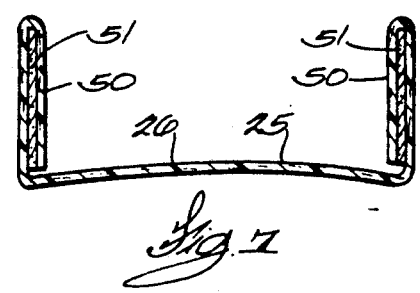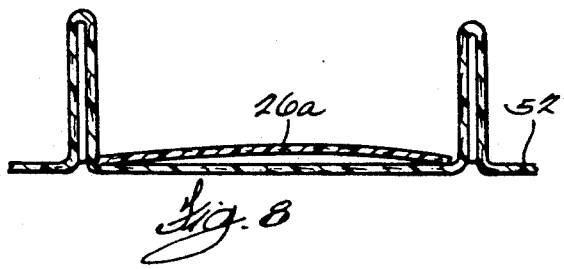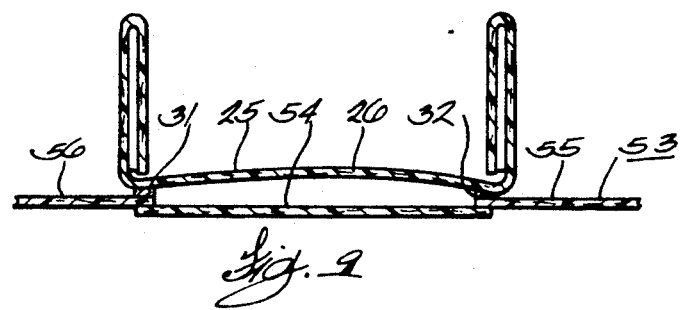

DIAPER WITH SOURCE REDUCTION OVERLAY AND HAVING IMPROVED FECAL CONTAINMENT CHARACTERISTICS

This application is a continuation-in-part of U.S. application Ser. No. 07/472,052 filed Jan. 31, 1990, now abandoned.

BACKGROUND OF THE INVENTION

Disposable baby diapers have been on the market for 40 years, but for the first 15 of those, the most popular version was the European two-piece, or Swedish diaper, which had a plastic pant arrangement with a separate removable and disposable absorbent pad or core.

In the mid-1960's, Procter & Gamble Company developed and effectively commercialized the one-piece disposable diaper having a rectangular absorbent pad with an integral plastic backing sheet folded into a "wing"-shape and marketed under the trademark "PAMPERS". Such a product is illustrated by the Duncan U.S. Pat. No. 3,180,335.

Ten years later, in the mid-1970's, the shaped elastic leg diaper became popular and has dictated the baby diaper development for the last 15 years. This product is illustrated by the Buell U.S. Pat. No. 3.860,003.

During the last few years, at least nine specific significant changes have been made to the disposable baby diaper:

1) Dry-touch covers with transport sub-layers (Meyer U.S. Pat. No. 4,798,603).
2) Frontal tapes with fit guides (Hirotsu U.S. Pat. No. 4,662,875).
3) Elastic waist bands (Kievit U.S. Pat. No. 4,515,595).
4) Multistrand elastic legs (Suzuki U.S. Pat. No. 4,425,127).
5) Superabsorbent cores (Weisman U.S. Pat. No. 4,610,678)
6) Leakage control end dams (Woon U.S. Pat. No. 4,296,750).
7) Stretchable tapes (Jacobs U.S. Pat. No. 3,800,796).
8) Gender specific cores (Weisman U.S. Pat. No. 4,673,402).
9) Fecal control cuffs (Enloe U.S. Pat. No. 4,704,116).

Of these improvements, the most recent and technically intriguing are the dry-touch cover and the fecal control cuffs.

The dry-touch cover creates a body-contacting surface which is hydrophobic and, therefore, presents no moisture against the body of the infant wearing the diaper. To accomplish this end-result, the covers have been made of plastic film or of carded, melt-blown, spun bonded or hydroentangled hydrophobic fibers, to permit rapid pass-through of the fluid to the diaper cores which have been made particularly and effectively absorbent, so that the fluid can be entrapped in the core. The core is designed so that it reduces as much as possible the wet-back of the fluid, under pressure, toward the body of the infant.

This dry-touch cover can also be made more effective by increasing the thickness of the coverstock material as shown in the Brock U.S. Pat. No. 4,766,029, or by the utilization of the Procter & Gamble perforated plastic film illustrated by the Thompson U.S. Pat. No. 3,929,135.

The thickness of the coverstock material can also be increased by utilizing high-loft fibers as shown in the Muhlratzer U.S. Pat. No. 4,761,323 or, as in the Kimberly-Clark Meyer U.S. Pat. No. 4,798603, by introducing one or more sub-layers of material between the coverstock and the core to draw the fluid away from the coverstock by capillary action.

The thicker the caliper of the web of the coverstock, the more expensive it becomes (because of material costs and production costs) and, quite frequently, it also becomes stiffer. All of this renders it less desirable than a lightweight, thin coverstock material.

As for the fecal control feature, changes to the early wing-fold "PAMPERS" included upstanding edges as shown in Schroeder U.S. Pat. No. 4,246,900 and Buell U.S. Pat. No. 4,636,207. The barrier "cuffs" were first commercialized in Japan as illustrated by the Suzuki U.S. Pat. No. 4,834,704 and Igaue U.S. Pat. No. 4,822,435. More recent diapers have featured the barriers shown in the Enloe U.S. Pat. No. 4,704,116 and the Lawson U.S. Pat. No. 4,695,278.

The effectiveness of such a construction is in its ability to contain feces (which generally do not penetrate into the absorbent core as does urine), by preventing the feces from spilling over the edge of the diaper, soiling the infant's garments or the surrounding environment.

Each of the features referred to above, particularly the dry-touch cover and the fecal containment cuffs have been developed independently of each other, and it is the object of the present invention to improve the performance by decreasing the wet-back of the diaper and, at the same time, by providing better fecal containment. This is done by providing a multi-ply coverstock of thin web material, one web of which also provides the fecal containment cuffs. The end result is that the cost of the coverstock is significantly reduced, the pass-through of the fluid from the body-side into the core is enhanced, the wet-back of the fluid from the core back to the body is reduced, the feces are kept on the diaper, and the overall performance of the diaper is enhanced.

As significant as is the design with regard to performance, it also is important in that it is a major step in the source reduction of waste and in the consumption of less raw material, and thus it reduces the adverse environmental impact of disposing of disposable diapers.

DESCRIPTION OF THE INVENTION

The disposable diaper of the present invention is generally similar to the shaped elastic leg products presently on the market, in that it includes (1) a backsheet which may be pervious to moisture vapor, but is impervious to fluid, (2) a topsheet which is in contact with the body of the infant and permits rapid pass-through of the urine into the absorbent core, and (3) an absorbent core, between the backsheet and the topsheet, which may be enhanced by the addition of superabsorbent materials or the like.

The diaper of the present invention, however, has a construction which provides better performance, because it does not have a sub-layer under the topsheet but, in fact includes an overlayer which improves the re-wet characteristics of the diaper without increasing the caliper of the coverstock material of which current diapers are made. Furthermore, there is a cost-improvement characteristic, because each of the layers of the multi-ply coverstock is less than half as thick as the conventional coverstock, and, in a major portion of the diaper, only one of the layers of the topsheet extends the full width of the diaper. The overlayer, which also includes the upstanding cuffs, is also narrower than the width of the conventional coverstock.

It is also important to note that in a diaper construction wherein the body-contacting portion is constructed of two thin layers of material rather than one thick layer, that the material degrades more effectively and quicker than does a single thick layer.

A significant characteristic of this diaper is that the space between the plys of the topsheet, where the plys are not bonded to each other, creates a structure which improves the dryness by decreasing the wetback of the fluid from the core to the body.

OBJECTS OF THE INVENTION

One object of the present invention is to provide an improved disposable baby diaper which has better performance characteristics, and which has less adverse environmental impact than previous disposable baby diapers.

Another object of the present invention is to provide a disposable baby diaper which consumes less raw materials than conventional baby diapers, and thus is economically more effective and more enviornmentally attractive.

Another object of the present invention is to provide a disposable baby diaper with improved wetback characteristics resulting from the use of an overlayer with unitary fecal control barriers or cuffs.

SUMMARY OF THE INVENTION

In the present invention, a disposable baby diaper is provided which has a well-known backsheet which may be pervious to gases, but which is impervious to liquids, a body-contacting topsheet or coversheet which is pervious, both to liquids and to gases, and an absorbent core which is disposed between the backsheet and the coversheet. It also includes the well-known tape-tabs for fastening the diaper around the body of the infant and may, selectively, also include a frontal tape or landing strip against which the tape tabs are secured; an elastic waistband mechanism at one or both ends of the diaper for enhancing the fit around the waist of the infant; one or more strands of leg elastication material which may be either rubber, LYCRA (a DuPont trademark) or polymer foam material for insuring that the diaper fits closely around the leg of the infant; absorbent-enhancing material within the core, such as superabsorbent granules or fibers; leakage control end dams at the waistband portions of the diaper and other submodifications such as stretchable tape-tabs or gender-specific absorbent core design.

In the present invention the coverstock is constructed of multi-ply material, one of which, preferably is less than half as thick as conventional coverstock, extends completely over the upper surface of the body-contacting surface of the diaper, is bonded to the backsheet around the periphery of the diaper, and which construction retains the core between the said ply and the backsheet.

Superimposed on the aforementioned coverstock ply is a second ply overlayer which preferably is the same material and thickness as the aforementioned first ply, but which is narrower, includes a pair of upstanding cuffs, and which is bonded to the aforementioned first ply only along the bottom edges of the upstanding cuffs so as to provide a space between the two plys, between the upstanding cuffs, where the two plys are not connected to each other and, therefore, provide improved wetback characteristic for the diaper.

With the above and other objects in view, more information and a better understanding of the present invention may be achieved by reference to the following detailed description.

DETAILED DESCRIPTION

For the purpose of illustrating the invention, there is shown in the accompanying drawings a form thereof which is at present preferred, although it is to be understood that the several instrumentalities of which the invention consists can be variously arranged and organized, and that the invention is not limited to the precise arrangements and organizations of the instrumentalities as herein shown and described.

FIG. 1 is a top plan view of the diaper of the present invention stretched out and lying flat and viewed against the topsheet.

FIG. 2 is a cross-sectional view taken generally along line 2—2 of FIG. 1.

FIG. 3 is a fragmentary vertical cross-sectional view taken generally along line 3—3 of FIG. 1.

FIG. 4 is a fragmentary cross-sectional view showing the assembly of the backsheet, the topsheet, the absorbent core, and the leg elastics.

FIG. 5 is a schematic vertical cross-sectional view of the upstanding cuffs and the overlayered portion of the topsheet of the present invention.

FIG. 5a is a schematic, vertical, cross-sectional view similar to FIG. 5 illustrating another version of the in-turned upper portion of the upstanding cuffs.

FIG. 5b is a schematic, vertical, cross-sectional view similar to FIGS. 5 and 5a, illustrating yet another means of providing the upper edge of the cuff with a "cushion".

FIG. 6 is a schematic cross-sectional view showing the combination of the views of FIGS. 4 and 5 showing the assembly of the multi-ply coverstock material.

FIG. 7 is a schematic, vertical, cross-sectional view similar to FIG. 5-a illustrating another form of cuff construction to render it impervious.

FIG. 8, like FIG. 5-a is yet another form of cuff construction with the overlayer formed separately from the cuffs.

FIG. 9 illustrates how the coverstock can be formed from a plurality of materials.

Referring now to FIG. 1, there is shown a disposable baby diaper 10, which includes an impervious backsheet 11 and a pervious topsheet 12 with an absorbent core 13 disposed between the topsheet and the backsheet.

The topsheet and the backsheet are generally joined together around the periphery of the core, either by thermobonding or by a light layer of adhesive 14, all as is well-known in the art.

One or more elastic strands 15, which may be made of rubber, laytex, LYCRA (a DuPont trademark), or an elastic foam material, extend through the crotch portion 16 of the diaper, generally outboard of the edges 17 of the core, in the crotch portion, but which may overlap the ears 18 of the core 13, as at 19, in the waistband portions 20 and 21.

By "outboard" is meant laterally beyond the longitudinal centerline of the diaper and preferably laterally beyond the longitudinal side edge of the core.

A plurality of refastenable tape members 22 are attached to the diaper in the rear waistband portion 20, as shown in FIGS. 1 and 2. These tape fasteners, when applied by the care-giver of the patient, or the mother of the baby, are generally fastened to the outer surface of the backsheet 11 in the front waistband portion 21 or, as more recently practiced, to a frontal tape (not shown) which enhances the refastenability of the taping system and also reinforces the frontal portion of the baby diaper.

Additionally, elastic waistband members 23 and 24 may be applied between the backsheet 11 and the coversheet 12 in the waistband portions 20 and 21, to enhance the fitting characteristics of the diaper.

Furthermore, leakage control barriers or "end dams" (not shown) may also be applied in lieu of elastic members 23 and 24, or in addition thereto, or may be combined as a portion of the elastic members 23 and 24 to reduce the likelihood of leakage of the urine at the ends of the waistband portions 20 and 21.

In the conventional baby diaper design, the coverstock 12 is generally a single ply of nonwoven material which may be made of carded fibers, either adhesively or thermally bonded, perforated plastic film, spun bonded fibers, or water entangled fibers, which generally weigh 0.7 oz./sq. yd. and having appropriate and effective machine-direction and cross-machine directional strength suitable for use as a baby diaper coverstock material.

However, in the diaper of the present invention, that portion of the coverstock material which completely overlies the diaper, as shown in FIG. 1, is made of a web weighing only 0.3 oz./sq. yd., but with increased cross-directional tensile strength and with improved fluid-transmitting characteristics and, therefore, costs less than half the price of conventional coverstock.

It will be noted, particularly, that the absorbent core 13, which has been made of absorbent fibers in a manner to produce a high integrity of the core, preferably does not have the customary or conventional creped tissue wadding wrapped around it and, therefore, the absence of that creped tissue material also decreases the cost of the diaper of the present invention.

The diaper of the present invention includes a second ply 25 of the lightweight (0.3 oz./sq. yd.) coverstock material. This portion of the multi-ply coverstock has a central area 26 which is narrower than the distance between the lateral edges 17 of the absorbent core, and which includes the upstanding portions 27 and 28 to provide the fecal containment area generally indicated at 29 in FIG. 2.

The upper portions 27a and 28a of the cuffs 27 and 28 are turned back upon themselves either inwardly or outwardly, and have disposed therebetween elastic strands 30a and 30b, which are adhesively secured to the upper edges of the cuffs 27 and 28 along the entire length thereof.

As is shown in FIG. 5, the upper edges of the cuffs 27 and 28 are turned outwardly as at 27a and 28a. In FIG. 5a, we have shown an alternative and preferred version where the upper portions are turned inwardly. This version, accomplishing the same end-result as the version shown in FIG. 5, nevertheless, provides a more comfortable body-contacting surface against the baby's bottom.

In FIG. 5b, we have also shown an alternative version of the upstanding cuff wherein the elastic strands 30a and 30b are spaced slightly below the uppermost edge of the cuffs 27 and 28. This provides a loop of material which acts as a "cushion" to soften the contact between the elastic strands 30a and 30b and the baby's body.

FIG. 7 shows how the cuffs can be formed when the inturned portion 50 of the cuff extends fully down to the central portion 26. The cuff is rendered impermable to all fluids either by applying a coating 51 of "BARRIER GUARD" (a trademark of I.G.I. Co.) hot melt material or securing a very thin plastic film such as polyethylene between the plys of the cuff.

FIG. 8 shows how the coverstock and the cuffs may be formed from a single piece 52 of web material, and the over-layer 26-a fastened thereto between the bases of the cuffs.

FIG. 9 is similar to FIG. 6 but illultrates how the coverstock 53 can be formed from a plurality of webs, the central portion 54 being pervious and the side portions 55,56 being impervious. In this embodiment the overlayer 26 and the cuffs 27,28 are formed in much the same manner as described in reference to FIGS. 5-a, 5-b and 7.

In all cases, the overlayer second ply 25 is secured to the first ply 12 at the edges 31 and 32, but not in the intervening area 33, thus to provide a "space" between the plys 12 and 25 which enhances the wetback characteristic (i.e., prevents fluid from flowing out of the core back through the plys into the contact with the baby's body) while yet, at the same time, increasing the spacing between the upper surface of the ply 25 and the absorbent core 13. This space effect is sometimes referred to as a "blousing" effect.

It is to be understood that the absence of any adhesive to bind these two plys together not only improves the wetback characteristic, but also enhances the economics of the diaper construction.

This construction increases the "pass-through" of the fluid from the infant to the core and restricts the return of the fluid from the core through the plys 12 and 25 where it would otherwise wet the baby's bottom and tend to create diaper rash.

The top layer of the diaper of the present invention can be either pre-assembled off-line, or, if made on-line, have a separate elastic unwind mechanism. This manufacturing flexibility allows elastic in the cuffs to have a different percentage of stretch than the leg elastic. This reduced stretch in the elasticating mechanism of the cuffs minimizes skin discomfort because it is less tightly in contact with the body of the baby.

Diapers made according to this concept have been proven to be satisfactory when there is an optimum stretch of 200% in the elastic strands 30a and 30b.

Additionally, we believe that the upstanding cuffs which have a vertical height, when stretched, in excess of $\frac{1}{4}$" but not exceeding 1", provide the optimum fecal control characteristic.

It will be noted particularly that the ends 34, 35, 36 and 37 of the elastic strands 30a and 30b terminate in the upstanding cuffs 27 and 28 at the ends thereof, and are, therefore, separated from the first ply 12 in the waistband areas 20 and 21.

This construction enables the elastic strands 30a and 30b more effectively to create a "pocket" between the upstanding cuffs 27 and 28 and the ends of the diaper in the waistband portion 20 and 21 by pulling the outer edges of the waistbnd ends 38 and 39 upwardly, as is shown at 40 in FIG. 3.

The second ply 25 of nonwoven material may, in the end portions 38 and 39 and the side portions 27b and 28b, be treated to render the material at that point impervious to fluid (i.e., impervious to both liquids and gases) without adversely affecting the perviousness or pass-through characteristics of the horizontal portion 26 between the fastening lines 31 and 32.

It is to be understood that the second ply 25 may be secured to the first ply 12 along the fastening line 31 and 32 by a thin bead of adhesive or by ultrasonic welding or any similar well-known method.

As is well known, environmental protocol starts with reduction of waste at the source, and in the present invention the use of a lesser quantity of non-woven material is an important way to improve the environment.

In addition to being a reduction of waste at the source, the two lighter-weight materials in the diaper of the present invention will degrade at a faster rate than one layer of nonwoven of basis weight equivalent to the two layers of the lighter weight nonwoven. Two layers of 0.3 oz./sq. yd. nonwoven will degrade under thermo, ultra-violet, composting, or landfill conditions at a faster rate than one layer of 0.6 oz/sq. yd. nonwoven.

We have also found that the use of a degradable adhesive like the "BARRIER GUARD" material of I.G.I. Nonwovens Division (Lyndhurst, N.J.) of THE INTERNATIONAL GROUP INC. improves the degradability of the entire diaper and, in addition to the source reduction advantage of the diaper of the present invention, aids in the ultimate disposability of the product after it has been used.

As an illustration of the economy of construction and, therefore, the improved positive impact on the environment, one can make a comparison with the consumption of nonwoven material in the diaper and a conventional diaper.

A conventional diaper generally uses a nonwoven web 12" wide of a basis weight of 0.7 oz./sq. yd. Therefore, a unit weight of this material is 8.4 oz./sq. yd.

In the present invention, the multi-ply web of 0.3 oz./sq. yd. material uses one layer or ply 12" wide and another one 8" wide, for a total of 20", or a unit weight of 0.6 oz./sq. yd. This is 71% of the normal consumption of nonwoven material and represents an environmental improvement because there is less raw material consumed at the source, and less nonwoven material to be disposed of with the soiled diaper.

In summary, the diaper of the present invention with the multi-ply coverstock material provides:

1) A better diaper performance, both in pass-through and in anti-wetback.
2) A cost and material savings because of the absence of crepe tissue around the core.
3) There is no sub-layer under the first ply portion of the coverstock.
4) The overlayer portion of the coverstock improves the re-wet characteristics without increasing (in fact, decreasing) the caliber of the coverstock.
5) Since coverstock material is generally sold in large volumes, there is a substantial cost reduction to the manufacturer of the diaper which can result in a reduced cost of the diaper to the mother.
6) The space between the plys of multi-ply coverstock improves the wetback.
7) The absence of adhesive between the two plys or the core-contaction ply improves the economics because there is no adhesive to be purchased for this application.

It is to be understood that the present invention may be embodied in other specific forms without departing from the spirit or special attributes hereof, and it is therefore desired that the presnt embodiments be considered in all respects as illustrative, and therefore not restrictive, reference being made to the appended claims rather than to the foregoing description to indicate the scope of the invention.

Having thus described our invention, what we claim as new and desire to protect by Letters Patent are the following:

1. A disposable absorbent pad such as a baby diaper or adult incontinent pad comprising:
   a backsheet having a width and a length,
   a multi-ply topsheet,
   a absorbent core, having lateral edges and end edges, located between said backsheet and said topsheet,
   the backsheet and the topsheet being secured together around the lateral edges and end edges of said core to hold said core therebetween,
   said multi-ply topsheet including a first ply having a width equal to the width of the backsheet and further including a second ply which overlies said first ply,
   said second ply having lateral edges defining a width narrower than the width of said first ply,
   said second ply being non-removably secured on top of said first ply along a pair of fastening lines spaced inwardly from the lateral edges of the core,
   said second ply having first elastic members secured under tension to its lateral edges,
   said first elastic members having ends,
   said lateral edges of said second ply being pulled upwardly and away from the first ply by said first elastic members such that said lateral edges of said second ply are located between said first elastic members and said fastening lines and are substantially perpendicular to said first ply,
   the ends of said first elastic members being unsecured to the first ply,
   said first ply and said second ply being unsecured to each other between the fastening lines to provide a gap therebetween.

2. A disposable absorbent pad of claim 1 wherein the lateral edges of said second ply include a portion folded back upon itself to create a tunnel in which said first elastic members are disposed.

3. A disposable absorbent pad of claim 2 wherein the second ply is formed of a fluid-pervious material between the lines wherein said second ply is secured to said first ply, said second ply being treated to render it impervious to both liquids and gases between the fastening lines and the lateral edges.

4. The pad of claim 3 wherein the second ply is treated with a thin coating of hot melt material.

5. A disposable absorbent pad of claim 4 wherein means for securing the backsheet and the topsheet to each other means for providing the fastening lines, and means for rendering the lateral edge of the second ply impervious, is a degradable adhesive.

6. The pad of claim 3 wherein the second ply is treated with a thin plastic film.

7. The pad of claim 6 wherein the thin plastic film is polyethylene.

8. A disposable absorbent pad of claim 2 wherein the portion of said lateral edge which is folded back upon itself is folded outwardly.

9. A disposable absorbent pad of claim 2 wherein the portion of said lateral edge which is folded back upon itself is folded inwardly.

10. A disposable absorbent pad of claim 1 wherein the width of the first ply plus the width of the second ply of the multi-ply top sheet is less than twice the width of the first ply of said multi-ply topsheet.

11. A disposable absorbent pad of claim 1 including second elastic members, said second elastic members secured under tension to said backsheet and topsheet outwardly of the lateral edges of said core.

12. A disposable absorbent pad of claim 11 wherein pulling upward of the lateral edges of said second ply by said first elastic members creates a tension in the second elastic members which is greater than the tension in the first elastic members secured along the lateral edges of the second ply.

13. A disposable absorbent pad of claim 1 wherein the first ply is a laminate which is made of a plurality of different non-woven materials.

14. A disposable absorbent pad of claim 13 wherein the first ply has a central pervious portion and an impervious portion secured along each side of the pervious portion.

15. A disposable absorbent pad of claim 1 wherein a portion of the first ply and a portion of the second ply, which are not secured to each other create a blousing effect between the first and second plys.

* * * * *